US006458357B1

(12) United States Patent
White et al.

(10) Patent No.: US 6,458,357 B1
(45) Date of Patent: Oct. 1, 2002

(54) RETRO-INVERSO NEUROTROPHIC AND ANALGESIC PEPTIDES

(75) Inventors: Michael T. White, La Jolla, CA (US); John S. O'Brien, La Jolla, CA (US); David E. Wright, Ramona, CA (US)

(73) Assignee: Myelos Corporation, San Diego, CA (US)

(*) Notice: Subject to any disclaimer, the term of this patent is extended or adjusted under 35 U.S.C. 154(b) by 0 days.

(21) Appl. No.: 09/148,030

(22) Filed: Sep. 3, 1998

Related U.S. Application Data

(63) Continuation-in-part of application No. 08/926,015, filed on Sep. 9, 1997, now abandoned.
(51) Int. Cl.[7] .................. A61K 39/00; A61K 38/00; A61K 38/16; A01N 37/18; C07K 14/00
(52) U.S. Cl. .................. 424/185.1; 514/2; 514/8; 530/300; 530/350
(58) Field of Search .................. 530/300, 350; 424/185.1; 514/2, 8

(56) References Cited

U.S. PATENT DOCUMENTS

| | | | |
|---|---|---|---|
| 4,234,571 A | * | 11/1980 | Nestor et al. |
| 4,560,505 A | | 12/1985 | Pinori et al. |
| 4,638,046 A | | 1/1987 | Verdini et al. |
| 4,713,367 A | | 12/1987 | Sisto et al. |
| 4,732,890 A | | 3/1988 | Bonelli et al. |
| 5,100,663 A | * | 3/1992 | Gottlieb |
| 5,218,089 A | | 6/1993 | Mariotti et al. |
| 5,498,694 A | * | 3/1996 | Ruoslahti |
| 5,529,914 A | | 6/1996 | Hubbell et al. |
| 5,571,787 A | | 11/1996 | O'Brien et al. |
| 5,723,452 A | | 3/1998 | Chan |
| 6,232,446 B1 | * | 5/2001 | Wallach et al. |

FOREIGN PATENT DOCUMENTS

WO  PCT/WO95/03821  2/1995

OTHER PUBLICATIONS

Rudinger et al (*Peptide Hormoves*, University Park Press, Pavsons et al editions pp. 1–7), Jun. 1976.*
O'Brien, et al., "Saposin proteins: structure, function, and role in human lysosomal storage disorders", The FASEB Journal 5:301–308, Mar. 1991.
Hiraiwa, et al., "Cell death prevention, mitogen–activated protein kinase stimulation, and increased sulfatide concentrations in Schwann cells and oligodendrocytes by prosaposin and prosaptides", Proc. Natl. Acad. Sci. USA 5:4778–4781, Apr. 1997.
Kishimoto, et al., "Saposins: structure, function, distribution, and molecular genetics", Journal of Lipid Research 33:1255–1267, 1992.

Kim, et al., "An experimental model for peripheral neuropathy produced by segmental spinal nerve ligation in the rat", Pain 50:355–363, 1992.
Banks, et al., "Permeability of the Blood–Brain Barrier to Peptides: An Approach to th eDevelopment of Therapeutically Useful Analogs", Peptides 13:1289–1294, 1992.
Mammi, et al., "Conformational Analysis of Cyclic Partially Modified Retro–Inverso Enkephalin Analogues by Proton NMR", Biochemistry 25:7607–7614, 1986.
Berman et al., "Receptor binding affinity and thermolysin degradation of truncated and retro–inverso–isomeric ANF analogs", Life Sciences 44:1267–1270, 1989.
Guichard, et al., "Partially Modified Retro–Inverso–Pseudopeptides as Non–natural Ligands for the Human Class I Histocompatibility Molecular HLA–A2" J. Med. Chem. 39:2030–2039, 1986.
Guichard, et al., "Antigenic mimicry of natural L–peptides with retro–inverso–peptidomimetics", Proc. Natl. Acad. Sci. USA 91:9765–9769, Oct. 1994.
Goodman, et al., :Synthesis and biological activity of linear and cyclic enkephalins modified at the $Gly^3$–$Phe^4$ amide bond, J. Peptide Protein Res. 25: 648–662, 1985.
Chorev, et al., "Recent developments in retro peptides and proteins—an ongoing topochemical exploration", TIBTECH reviews 13:438–445, 1995.
O'Brien, et al., "Identification of the neurotrophic factor sequence of prosaposin", The FASEB Journal 9:681–685, May 1995.
O'Brien, et al., "Identification of prosaposin as an neurotrophic factor", Proc. Natl. Acad. Sci. USA 91:9593–9596, Sep. 1994.
Hughes, et al., "Identification of two related pentapeptides from the brain with potent opiate agonist activity", Nature 258:577–579, Dec. 1975.
Momany, et alt.,, "Conformational Energy Analysis of Retro–All–D–Methionine Enkephalin", Biopolymers 17:2609–2615, 1978.
Doi, et al., "Conserved activity in Reverse Enantiomeric Opioid Peptide" Life Sciences 56(19):1557–1562, 1995.

* cited by examiner

*Primary Examiner*—Mark Navarro
(74) *Attorney, Agent, or Firm*—Kenyon & Kenyon

(57) ABSTRACT

Retro-inverso peptide analogs derived from the active neurotrophic region of saposin C. The saposin C-derived peptides (prosaptides) induce neurite outgrowth in vitro, prevent programmed cell death, induce myelination and have an analgesic effect. They are useful in the treatment of central and peripheral nervous system disorders and pain management. The retro-inverso peptides are significantly more resistant to metabolic degradation than the corresponding non-inverted peptides.

28 Claims, 11 Drawing Sheets

SEQUENCE LISTING

<160> NUMBER OF SEQ ID NOS: 12

<210> SEQ ID NO 1
<211> LENGTH: 22
<212> TYPE: PRT
<213> ORGANISM: Homo Sapien

<400> SEQUENCE: 1

Cys Glu Phe Leu Val Lys Glu Val Thr Lys Leu Ile Asp Asn Asn Lys
1               5                   10                  15

Thr Glu Lys Glu Ile Leu
            20

<210> SEQ ID NO 2
<211> LENGTH: 18
<212> TYPE: PRT

```
<213> ORGANISM: Homo Sapien

<400> SEQUENCE: 2

Tyr Lys Glu Val Thr Lys Leu Ile Asp Asn Asn Lys Thr Glu Lys Glu
1               5                   10                  15

Ile Leu

<210> SEQ ID NO 3
<211> LENGTH: 12
<212> TYPE: PRT
<213> ORGANISM: Homo Sapien

<400> SEQUENCE: 3

Leu Ile Asp Asn Asn Lys Thr Glu Lys Glu Ile Leu
1               5                   10

<210> SEQ ID NO 4
<211> LENGTH: 14
<212> TYPE: PRT
<213> ORGANISM: Homo Sapien
<220> FEATURE:
<221> NAME/KEY: MOD_RES
<222> LOCATION: (2)...(2)
<223> OTHER INFORMATION: D-Ala

<400> SEQUENCE: 4

Thr Xaa Leu Ile Asp Asn Asn Ala Thr Glu Glu Ile Leu Tyr
1               5                   10

<210> SEQ ID NO 5
<211> LENGTH: 14
<212> TYPE: PRT
<213> ORGANISM: Homo Sapien
<220> FEATURE:
<221> NAME/KEY: MOD_RES
<222> LOCATION: (1)...(14)
<223> OTHER INFORMATION: All D amino acids

<400> SEQUENCE: 5

Tyr Leu Ile Glu Glu Thr Ala Asn Asn Asp Ile Leu Ala Thr
1               5                   10

<210> SEQ ID NO 6
<211> LENGTH: 14
<212> TYPE: PRT
<213> ORGANISM: Homo Sapien

<400> SEQUENCE: 6

Ser Glu Leu Ile Ile Asn Asn Ala Thr Glu Glu Leu Leu Tyr
1               5                   10

<210> SEQ ID NO 7
<211> LENGTH: 12
<212> TYPE: PRT
<213> ORGANISM: Homo Sapien
<220> FEATURE:
<221> NAME/KEY: MOD_RES
<222> LOCATION: (1)...(12)
<223> OTHER INFORMATION: All D amino acids

<400> SEQUENCE: 7

Tyr Leu Leu Glu Glu Thr Ala Asn Asn Asp Leu Leu
1               5                   10

<210> SEQ ID NO 8
<211> LENGTH: 11
```

```
<212> TYPE: PRT
<213> ORGANISM: Rattus
<220> FEATURE:
<221> NAME/KEY: MOD_RES
<222> LOCATION: (1)...(11)
<223> OTHER INFORMATION: All D amino acids

<400> SEQUENCE: 8

Leu Leu Glu Glu Thr Ala Asn Asn Asp Leu Leu
1               5                   10

<210> SEQ ID NO 9
<211> LENGTH: 15
<212> TYPE: PRT
<213> ORGANISM: Homo Sapien
<220> FEATURE:
<221> NAME/KEY: MOD_RES
<222> LOCATION: (2)...(2)
<223> OTHER INFORMATION: D-Ala

<400> SEQUENCE: 9

Thr Xaa Leu Ile Asp Asn Asn Lys Thr Glu Lys Glu Ile Leu Tyr
1               5                   10                  15

<210> SEQ ID NO 10
<211> LENGTH: 15
<212> TYPE: PRT
<213> ORGANISM: Homo Sapien

<400> SEQUENCE: 10

Thr Lys Leu Ile Asp Asn Asn Lys Thr Glu Lys Glu Ile Leu Asp
1               5                   10                  15

<210> SEQ ID NO 11
<211> LENGTH: 13
<212> TYPE: PRT
<213> ORGANISM: Homo Sapien
<220> FEATURE:
<221> NAME/KEY: MOD_RES
<222> LOCATION: (1)...(13)
<223> OTHER INFORMATION: All D amino acids

<400> SEQUENCE: 11

Tyr Leu Glu Glu Thr Ala Asn Asn Asp Leu Leu Ala Thr
1               5                   10

<210> SEQ ID NO 12
<211> LENGTH: 11
<212> TYPE: PRT
<213> ORGANISM: Homo Sapien
<220> FEATURE:
<221> NAME/KEY: MOD_RES
<222> LOCATION: (1)...(2)
<223> OTHER INFORMATION: Any D amino acid
<221> NAME/KEY: MOD_RES
<222> LOCATION: (3)...(4)
<223> OTHER INFORMATION: D-Lys, D-Arg, D-His, D-Asp or D-Glu
<221> NAME/KEY: MOD_RES
<222> LOCATION: (6)...(9)
<223> OTHER INFORMATION: Any D amino acid
<221> NAME/KEY: MOD_RES
<222> LOCATION: (10)...(10)
<223> OTHER INFORMATION: absent, Leu or Ile
<221> NAME/KEY: MOD_RES
<222> LOCATION: (11)...(11)
<223> OTHER INFORMATION: Leu or Ile
```

```
<400> SEQUENCE: 12

Xaa Xaa Xaa Xaa Thr Xaa Asn Asn Xaa Xaa Xaa
 1               5                  10
```

RETRO-INVERSO NEUROTROPHIC AND ANALGESIC PEPTIDES

RELATED APPLICATION

This application is a continuation-in-part of U.S. application Ser. No. 8/926,015, filed Sep. 9, 1997, now obtained the entire contents of which are hereby incorporated by reference.

FIELD OF THE INVENTION

The present invention relates to neurotrophic and analgesic peptides and their methods of use. More specifically, the invention relates to stable, active retro-inverso analogs of neurotrophic peptide fragments of saposin C.

BACKGROUND OF THE INVENTION

Demyelination is a defect common to a number of central nervous system (CNS) disorders, the most prevalent being multiple sclerosis (MS). MS, a chronic disorder which may lead to total disability, is characterized by damage to the myelin sheath, leaving the axons mostly intact. MS is the most prevalent neurological disease of young adults. The incidence of MS in the United States is approximately 300,000. Currently, the treatment for MS using anti-inflammatory drugs is palliative rather than curative; reversal of demyelination is minimal since these drugs act to reduce inflammation rather than promote repair (*Interferon Therapy of Multiple Sclerosis*, Reder, A. ed., Marcel Dekker, New York, 1997). Other central nervous system disorders involving demyelination include acute disseminated encephalomyelitis, trauma to brain and/or spinal cord, acute hemorrhagic leukodystrophy, progressive multifocal leukoencephalitis, metachromatic leukodystrophy, adrenal leukodystrophy and maldevelopment of the white matter in premature infants (periventricular leucomalacia). The peripheral nervous system (PNS) can also undergo demyelination, such as that occurring in Guillain-Barré syndrome (*Pathologic Basis of Disease*, Robbins et al. eds., W. B. Saunders, Philadelphia, 1979, pp. 1578–1582), traumatic injury and inflammatory or infectious neuropathies. Peripheral nerve injuries and peripheral neuropathies, such as those resulting from diabetes or chemotherapy, comprise the most prevalent peripheral nervous system disorders.

Neurotrophins and neurotrophic factors are proteins or peptides capable of affecting the survival, target innervation and/or function of neuronal cell populations (Barde, *Neuron*, 2:1525–1534, 1989). The efficacy of neurotrophins both in vivo and in vitro has been well documented. For example, nerve growth factor (NGF) acts as a trophic factor for forebrain cholinergic, peripheral and sensory neurons (Hefti et al., *Neurobiol. Aging*, 10:515–533, 1989). In vivo experiments indicate that NGF can reverse naturally-occurring as well as physical traumatic injuries to peripheral nerves (Rich et al., *J. Neurocytol.*, 16:261–268, 1987). Brain-derived neurotrophic factor (BDNF) is a trophic factor for peripheral sensory neurons, dopaminergic neurons of the substantia nigra, central cholinergic neurons and retinal ganglia (Henderson et al., *Restor. Neurol. Neurosci.*, 5:15–28, 1993). BDNF has been shown to prevent normally-occurring cell death both in vitro and in vivo (Hofer et al., *Nature*, 331:261–262, 1988). Ciliary neurotrophic factor (CNTF) promotes survival of chicken embryo ciliary ganglia in vitro and supports survival of cultured sympathetic, sensory and spinal motor neurons (Ip et al., *J. Physiol. Paris*, 85:123–130, 1991).

Prosaposin is the precursor of a group of four small heat-stable glycoproteins which are required for hydrolysis of glycosphingolipids by lysosomal hydrolases (Kishimoto et al., *J. Lipid Res.* 33:1255–1267, 1992). Prosaposin is proteolytically processed in lysosomes, generating saposins A, B, C and D (O'Brien et al., *FASEB J.*, 5:301–308, 1991). O'Brien et al. (*Proc. Natl. Acad. Sci. U.S.A.*, 91:9593–9596, 1994), U.S. Pat. No. 5,571,787 and published PCT Application No. WO95/03821, the entire contents of which are hereby incorporated by reference, disclose that prosaposin and saposin C stimulate neurite outgrowth and promote increased myelination. In addition, U.S. Pat. No. 5,571,787 and WO95/03821 disclose that a 22-mer peptide (CEFLVKEVTKLIDNNKTEKEIL; SEQ ID NO: 1) consisting of amino acids 8–29 of human saposin C stimulates neurite outgrowth in both neuroblastoma cells and mouse cerebellar explants. These references also disclose that an 18-mer peptide (YKEVTKLIDNNKTEKEIL; SEQ ID NO: 2) contained within the active 22-mer of saposin C (with V replaced by Y) also promotes neurite outgrowth and was able to cross the blood-brain barrier. O'Brien et al. (*FASEB J.*, 9:681–685, 1995) show that the 22-mer stimulates choline acetyltransferase activity and prevented cell death in neuroblastoma cells in vitro. The active neuritogenic fragment was localized to a linear 12-mer located in the amino-terminal sequence of saposin C (LIDNNKTEKEIL; SEQ ID NO: 3). The 22-mer (SEQ ID NO: 1) is a loop at the adjacent asparagine residues flanked by helical regions in native prosaposin.

A major obstacle to the in vivo therapeutic use of peptides is their susceptibility to proteolytic degradation. Retro-inverso peptides are isomers of linear peptides in which the direction of the sequence is reversed (retro) and the chirality, D or L, of each amino acid is inverted (inverso). There are also partially modified retro-inverso isomers of linear peptides in which only some of the peptide bonds are reversed and the chirality of the amino acid residues in the reversed portion is inverted. The major advantage of such peptides is their enhanced activity in vivo due to improved resistance to proteolytic degradation (For review, see Chorev et al., *Trends Biotech.*, 13:438–445, 1995). Although such retro-inverso analogs exhibit increased metabolic stability, their biological activity is often greatly compromised (Guichard et al., *Proc. Natl. Acad Sci. U.S.A.*, 91:9765–9769, 1994). For example, Richman et al. (*J. Peptide Protein Res.*, 25:648–662) determined that analogs of linear and cyclic leu-enkephalin modified at the Gly$^3$-Phe$^4$ amide bond had activities ranging from 6%–14% of native leu-enkephalin. Chorev et al., (ibid.) showed that retro-inversion of a peptide which inhibits binding of vitronectin to its receptor resulted in one peptide which was less potent than the parent isomer by a factor of 50,000, and another peptide which was 4,000 fold more potent than the parent cyclic peptide. Guichard et al. (*TIBTECH* 14, 1996), teach that retro-inverso (all-D-retro) antigenic mimicry may only occur with peptides in random coil, loop or cyclic conformations. In the case of "helical" peptide, adequate functional mimicry would be expected only if the helicity was, in fact, absent under the solvent conditions used for asessing antigenic mimicry.

There is a need for neurotrophic and analgesic peptides exhibiting increased metabolic stability while retaining biological activity. The present invention addresses this need.

SUMMARY OF THE INVENTION

The present invention includes the discovery that retro-inverted peptides of neurotrophic saposin C fragments have a surprisingly high level of neurotrophic activity. Modified and substituted versions of these peptides are also surprisingly active, and are stable in vivo. Simple screening protocols are set forth hereinbelow to enable rapid determination of activity for any particular candidate peptide. Although retro-inverted peptides have, in the past, had poor activity, the present invention illustrates that the retro-inverso approach is ideally suited for neurotrophic fragments of saposin C.

One embodiment of the present invention is a peptide having between 10 and about 40 amino acids, wherein the peptide includes the amino acid sequence shown in SEQ ID NO: 12. Preferably, the peptide has the sequence shown in SEQ ID NOS: 5, 7, 8 or 11. Preferably, the peptide is modified at the amino terminus, carboxy terminus, or both amino and carboxy terminus with one of the following independently selected moieties: $CH_3CO$, $CH_3(CH_2)_nCO$, $C_6H_5CH_2CO$ and $H_2N(CH_2)_nCO$, wherein n=1–10. Advantageously, the peptide is glycosylated at Asn7 or at the alpha amino group. In one aspect of this preferred embodiment, one or more amide bonds of the peptide is reduced. In another aspect of this preferred embodiment, one or more nitrogens in the peptide is methylated. Preferably, one or more carboxylic acid groups in the peptide is esterified.

The present invention also provides a method for stimulating neuritogenesis or preventing neural cell death, comprising the step of contacting neural cells with a composition comprising an effective neuritogenic or neural cell death-preventing amount of a peptide having between 11 and about 40 amino acids, wherein the peptide includes the amino acid sequence shown in SEQ ID NO: 12. Preferably, the neuronal cells are neuroblastoma cells. Advantageously, the neuroblastoma cells are NS20Y cells.

Another embodiment of the present invention is a method for stimulating myelination or preventing demyelination, comprising the step of contacting neural cells with a composition comprising an effective myelin-stimulating or demyelination-inhibiting amount of a peptide having between 11 and about 40 amino acids, wherein said peptide includes the amino acid sequence shown in SEQ ID NO: 12. Preferably, the peptide has the sequence selected shown in SEQ ID NOS: 5, 7, 8 or 11.

The present invention also provides a method for treating pain in a mammal in need thereof, comprising administering to the mammal an effective pain-treating amount of a composition comprising a peptide having between 11 and about 40 amino acids, wherein the peptide includes the amino acid sequence shown in SEQ ID NO: 12. Preferably, the peptide has the sequence shown in SEQ ID NOS: 5, 7, 8 or 11.

The present invention also provides a pharmaceutical composition comprising a peptide having between 11 and about 40 amino acids, wherein the peptide includes the sequence shown in SEQ ID NO: 12, in a pharmaceutically acceptable carrier. Preferably, the composition is in a controlled release formulation. Alternatively, the composition is in liposomal form. The composition may also be in lyophilized form. Preferably, the composition is in unit dosage form.

The present invention also provides a method for stimulating myelination or inhibiting demyelination in a mammal in need thereof, comprising the step of administering to the mammal a composition comprising an effective myelin-stimulating or demyelination-inhibiting amount of a peptide having between 10 and about 40 amino acids, wherein the peptide includes the amino acid sequence shown in SEQ ID NO: 12. preferably, the peptide has the sequence shown in SEQ ID NOS: 5, 7, 8 or 11. Advantageously, the administering step comprises intravenous, pulmonary, intrathecal, intramuscular, intradermal, subcutaneous, intracranial, epidural, topical and oral.

DETAILED DESCRIPTION OF THE PREFERRED EMBODIMENTS

The present invention includes the discovery that like the native peptide fragments, retro-inverted (RI) peptides encompassing the active neurotrophic region of saposin C stimulate neurite outgrowth and prevent neural cell death. These peptides also promote increased myelination in neural cells. This result is surprising because it was unlikely that the retro-inverso analogs would adopt the same confirmation required for binding to the prosaposin receptor as the corresponding all L-native peptide, especially in view of Guichard et al., 1996 (supra.) who teach that retro-inverso peptides containing large proportions of helical structure would not be expected to have adequate functional mimicry.

A native 15-mer (TKLIDNNKTEKEILD; SEQ ID NO: 10) contained within human saposin C and encompassing the active neurite-promoting region shown in SEQ ID NO: 3 (LIDNNKTEKEIL) was modified as follows to decrease its susceptibility to proteolysis in vivo: Lys 2 was replaced with D-ala to increase resistance to exopeptidases; lys 8 was replaced with ala to increase resistance to trypsin digestion; and lys 11 was deleted to increase resistance to trypsin digestion. In addition, asp 15 was replaced with tyr to provide an iodination site. Thus, the resulting peptide, TX14(A), contained no cleavage sites for trypsin or chymotrypsin. Retro-inverted TX14(A) (Peptide D2) contained the amino acids of TX14(A) in reverse order and all residues had the D chirality to further minimize susceptibility to proteolytic degradation.

Figure 1:
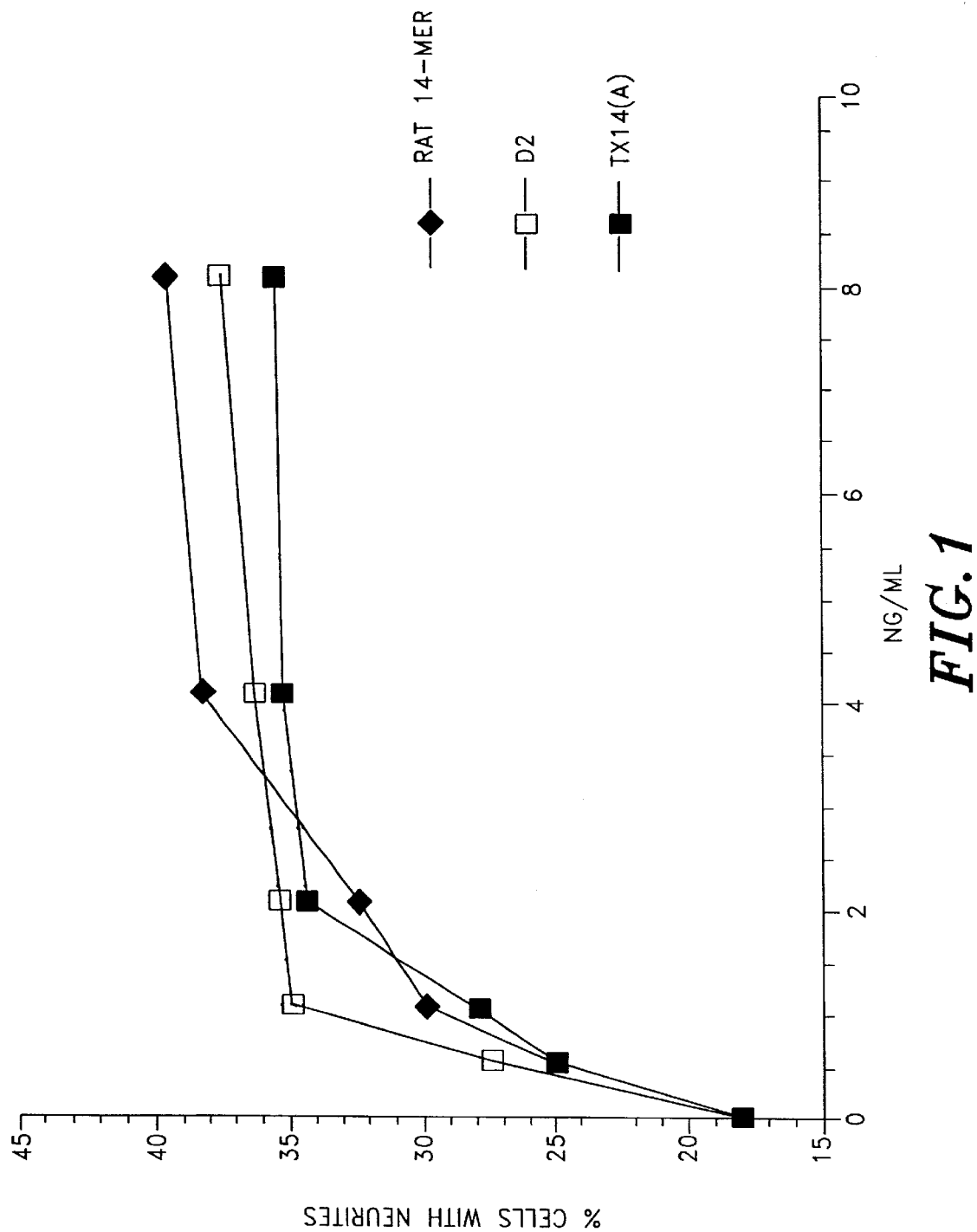
FIG. 1 illustrates a NS20Y neuroblastoma neurite outgrowth assay using peptides TX14(A) (TXLIDNNATEEILY, X=D-alanine; SEQ ID NO: 4), Retro-inverted TX14(A) (Peptide D2; YLIEETANNDILAT, all D-amino acids; SEQ ID NO: 5) and a rat 14-mer derived from the saposin C active sequence (SELIINNATEELLY; SEQ ID NO: 6).
Figure 2:
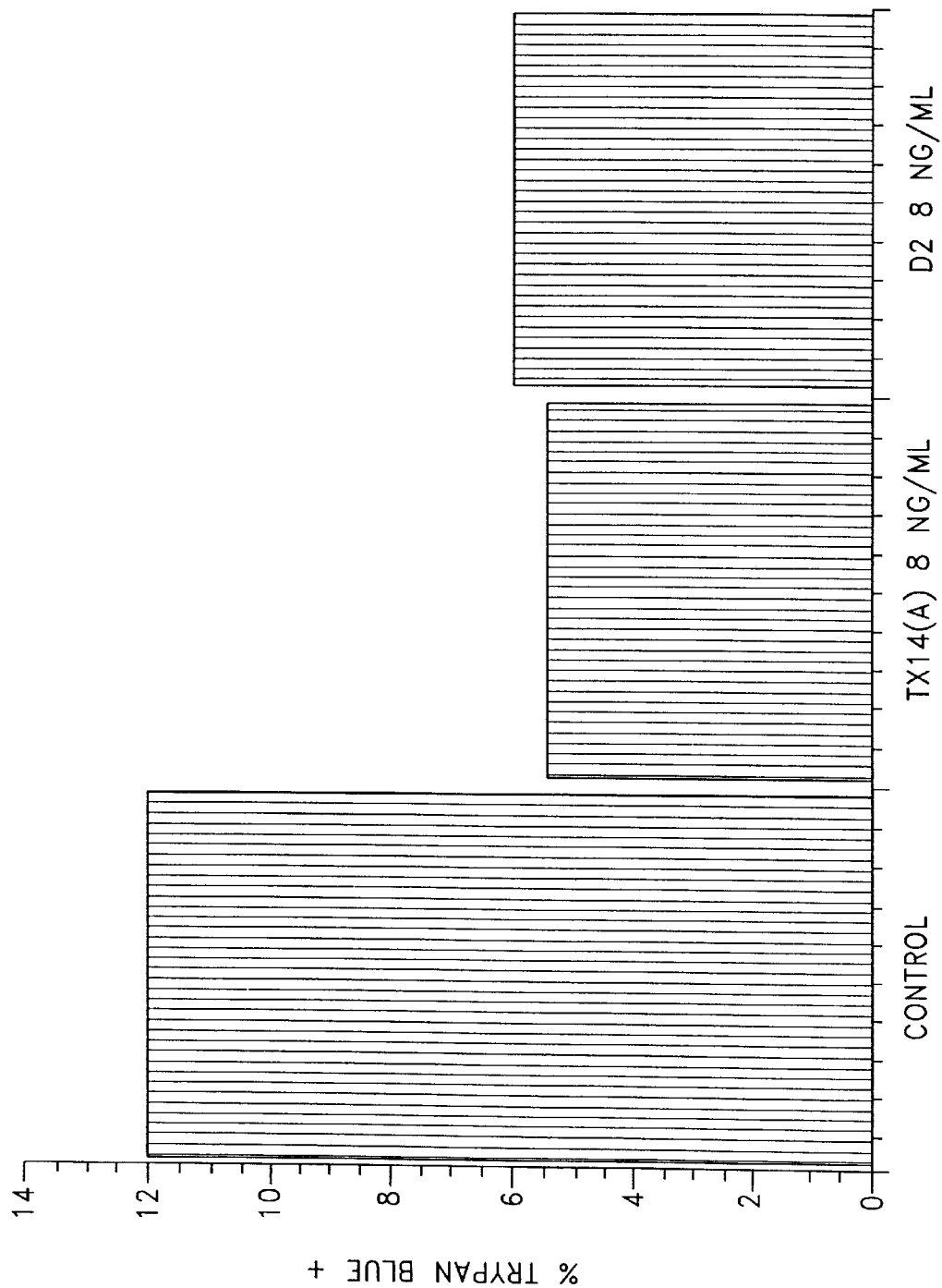
FIG. 2 illustrates a cell death assay using NS20Y neuroblastoma cells. NS20Y cells were grown for 48 hours in low serum in the presence or absence of effector peptides and dead cells were identified by Trypan blue staining.
Figure 3:
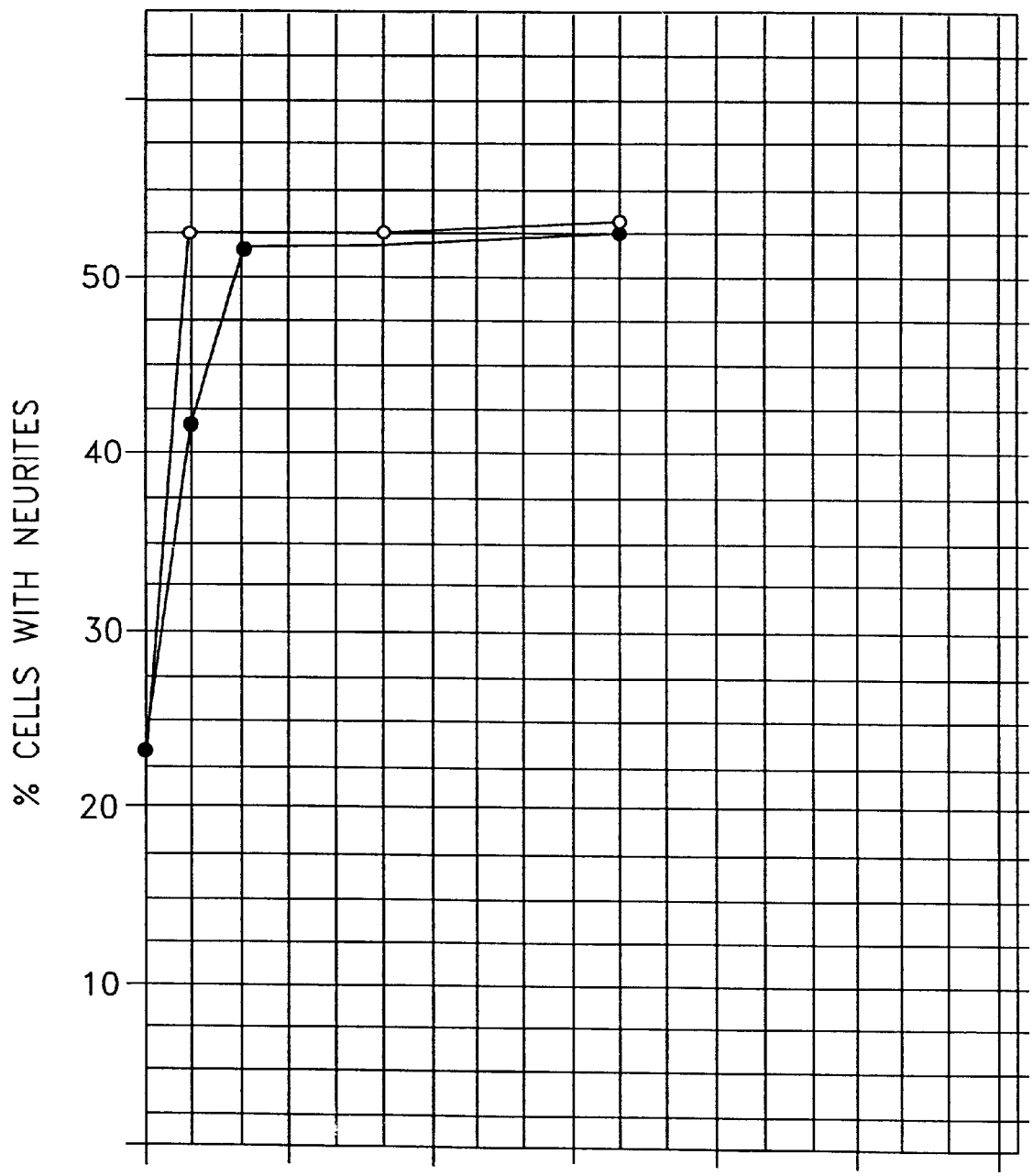
FIG. 3 illustrates a NS20Y neurobastoma neurite outgrowth assay using peptide D4 (YLLEETANNDLL, all D-amino acids; SEQ ID NO: 7) and peptide D5 (LLEETANNDLL, all D-amino acids; SEQ ID NO: 8).

Peptides TX14(A), D2, D4 and D5 all exhibited neuritogenic activity in in vitro neurite outgrowth assays (FIGS. 1 and 3). In fact, peptide D2, the RI peptide, was slightly more active that TX14(A) (FIG. 1). Peptides D4 and D5 were also somewhat more active than TX14(A). Peptides TX14(A) and D2 also prevented cell death in neuroblastoma cells in culture to the same extent (FIG. 2). Another retro-inverso peptide, D3 (YLEETANNDLLAT; SEQ ID NO: 11) also promoted neurite outgrowth in vitro.

Importantly, as shown in Example 5, systemic administration of peptide D5 reduces lesion severity in an EAE model in the Lewis rat by direct action on the remyelination process. This action differs from the anti-inflammatory effect of current MS drugs which act to reduce inflammation by action on macrophages. Any desired peptide comprising the sequence shown in SEQ ID NO: 12 can be tested in this model to determine its ability to reverse demyelination, or in any of the other assays described herein to determine its ability to promote neurite outgrowth and myelination. Functional return was demonstrated by the return of stride length of the treated animals to normal. Stride length is a measure of extremity weakness.

Completely or partially RI saposin C-derived peptides comprising the RI active 11-mer sequence shown in SEQ ID NO: 8, or comprising the consensus sequence shown in SEQ ID NO: 12 below, and neurotrophic and/or myelinotrophic analogs thereof, possess significant therapeutic applications in promoting functional recovery after toxic, traumatic, ischemic, degenerative and inherited lesions to the peripheral and central nervous system. In addition, these RI peptides stimulate myelination and counteract the effects of demyelinating diseases. These peptides stimulate the outgrowth of neurons, promote myelination and prevent programmed cell death in neuronal tissues of myelinating glia, i.e. oligodendrocytes. The RI saposin C-derived peptides of the invention are also useful as analgesics, particularly for the treatment of neuropathic pain which can develop days or months after a traumatic injury and is often long-lasting or chronic. SEQ ID NO: 8 may be modified as follows and still retain neurotrophic activity: Leu1 and Leu2 can be any amino acid; Glu3 and Glu 4 can be any charged amino acid (lys, arg, his, asp, or glu); Thr 5 is essential; Ala6 can be any amino acid; Asn7 and Asn8 are essential; Asp9 is any amino acid; and Leu10 is leucine or isoleucine. This, along with the sequences of RI peptides D2 and D3, produce the following consensus sequence (all D-amino acids):

$$X_1X_2X_3X_4TX_5NNX_6X_7X_8$$ (SEQ ID NO: 12)

in which $X_1$ and $X_2$ are any amino acid; $X_3$ and $X_4$ are lysine, arginine, histidine, aspartic acid or glutamic acid; T is threonine; $X_5$ is any amino acid; N is asparagine; $X_6$ is any amino acid; $X_7$ is absent, leucine or isoleucine; and $X_8$ is leucine or isoleucine. An active RI fragment of prosaposin preferably has about 10 amino acids to about 40 amino acids. Preferably, an active RI fragment derived from prosaposin has about 10 amino acids to about 22 amino acids.

One embodiment of the present invention is a method of facilitating neurite outgrowth in differentiated or undifferentiated neural cells by administering to the cells an effective, neurite outgrowth-facilitating amount of a RI saposin C-derived peptide encompassing the RI active 11-mer region shown in SEQ ID NO: 8 or analogs thereof as defined in SEQ ID NO: 12. Such analogs further include, for example, replacement of one or more lysine and/or arginine residues with alanine or another amino acid; deletion of one or more lysine and/or arginine residues; replacement of one or more tyrosine and/or phenylalanine residues, deletion of one or more phenylalanine residues and conservative replacements of one or more amino acids within the peptide. The replacement or deletion of lysine/arginine and tyrosine/phenylalanine residues will reduce the susceptibility of peptide degradation by trypsin and chymotrypsin, respectively.

Additional variations of these peptide sequences contemplated for use in the present invention include minor insertions and deletions. Conservative amino acid replacements are contemplated. Such replacements are, for example, those that take place within a family of amino acids that are related in the chemical nature of their side chains. The families of amino acids include the basic charged amino acids (lysine, arginine, histidine); the acidic charged amino acids (aspartic acid, glutamic acid); the non-polar amino acids (alanine, valine, leucine, isoleucine, proline, phenylalanine, methionine, tryptophan); the uncharged polar amino acids (glycine, asparagine, glutamine, cysteine, serine, threonine, tyrosine); and the aromatic amino acids (phenylalanine, tryptophan and tyrosine). In particular, it is generally accepted that conservative amino acid replacements consisting of an isolated replacement of a leucine with an isoleucine or valine, or an aspartic acid with a glutamic acid, or a threonine with a serine, or a similar conservative replacement of an amino acid with a structurally related amino acid will not have a major effect on the properties of the peptide. The ability of any RI peptide comprising the sequence shown in SEQ ID NO: 12, or insertions, deletions or substitutions thereof, to promote neurite outgrowth, myelination, and reverse demyelination and prevent neural cell death can be determined using the assays provided in the examples presented below.

Various standard chemical modifications will improve the stability, bioactivity and ability of the peptide to cross the blood brain barrier. One such modification is aliphatic amino terminal modification with a derivative of an aliphatic or aromatic acid, forming an amide bond. Such derivatives include, for example, $CH_3CO$, $CH_3(CH_2)_nCO$ (n=1–10), $C_6H_5CH_2CO$, $H_2N-(CH_2)_nCO$ (n=1–10). Another modification is carboxy terminal modification with a derivative of an aliphatic or aromatic amine/alcohol coupled to the peptide via an amide/ester bond. Such derivatives include those listed above. The peptides may also have both amino and carboxy terminal modifications, wherein the derivatives are independently selected from those listed above. The peptides may also be glycosylated, wherein either the alpha amino group or the D-Asn 8 of the peptide shown in SEQ ID NO: 12, or both, are modified with glucose or galactose. In another contemplated modification, selected backbone amide bonds are reduced ($-NH-CH_2$). Other modifications include N-methylation of selected nitrogens in the amide bonds and esters in which at least one of the acid groups on the peptide are modified as aromatic or aliphatic esters. Any combination of the above modifications is also contemplated.

The ability of any such peptide to stimulate neurite outgrowth or to act as opiate receptor agonists can easily be determined by one of ordinary skill in the art using the procedures described in Examples 1 and 2 hereinbelow.

A typical minimum amount of the RI peptide for the neurotrophic activity in cell growth medium is usually at least about 5 ng/ml. This amount or more of the RI peptides of the invention for in vitro use is contemplated. Typically, concentrations in the range of 0.1 µg/ml to about 10 µg/ml of these peptides will be used. Effective amounts for any particular tissue can be determined in accordance with Example 1.

The neural cells can be treated in vitro or ex vivo by directly administering the RI peptides of the invention to the cells. This can be done, for example, by culturing the cells in growth medium suitable for the particular cell type followed by addition of the peptide to the medium. When the cells to be treated are in vivo, typically in a vertebrate, preferably a mammal, the composition can be administered by one of several techniques. Most preferably, the composition is injected directly into the blood in sufficient quantity to give the desired local concentration of peptide. These RI peptides persist longer in vivo due to the D peptide bonds. In the peptides lacking lysine and arginine residues, proteolytic degradation is reduced.

The smaller peptides (i.e. 50-mer or less) will most likely cross the blood brain barrier and enter the central nervous system for treatment of CNS disorders (see Banks et al., *Peptides*, 13:1289–1294, 1992). In fact, significant amounts of peptide D4 were present in the brain after intramuscular injection into a rat.

For treatment of neural disorders, direct intracranial injection or injection into the cerebrospinal fluid may also be used in sufficient quantities to give the desired local concentration of neurotrophin. In both cases, a pharmaceutically acceptable injectable carrier is used. Such carriers include, for example, phosphate buffered saline and Ringer's solution. Alternatively, the composition can be administered to peripheral neural tissue by direct local injection or by systemic administration. Various conventional modes of administration are contemplated including intravenous, pulmonary, intramuscular, intradermal, subcutaneous, intracranial, epidural, intrathecal, topical and oral. For use as an analgesic, administration by direct intravenous injection is preferred.

The neurotrophic and analgesic peptide compositions of the invention can be packaged and administered in unit dosage form such as an injectable composition or local preparation in a dosage amount equivalent to the daily dosage administered to a patient or as a controlled release composition. A septum sealed vial containing a daily dose of the active ingredient in either PBS or in lyophilized form is an example of a unit dosage. In a preferred embodiment, daily systemic dosages of the RI peptides of the invention based on the body weight of the vertebrate for treatment of neural diseases or as an analgesic are in the range of from about 0.01 to about 10,000 µg/kg. More preferably, daily systemic dosages are between about 0.1 and 1,000 µg/kg. Most preferably, daily systemic dosages are between about 10 and 100 µg/kg. Daily dosages of locally administered material will be about an order of magnitude less. Oral administration is particularly preferred because of the resistance of the peptides to proteolytic degradation in the gastrointestinal system.

In one preferred embodiment of the invention, the neurotrophic peptides are administered locally to neural cells in vivo by implantation thereof. For example, polylactic acid, polygalactic acid, regenerated collagen, multilamellar liposomes and many other conventional depot formulations comprise bioerodible or biodegradable materials that can be formulated with biologically active neurotrophic peptide compositions. These materials, when implanted, gradually break down and release the active material to the surrounding tissue. The use of bioerodible, biodegradable and other depot formulations is expressly contemplated in the present invention. Infusion pumps, matrix entrapment systems and combination with transdermal delivery devices are also contemplated. The peptides may also be encapsulated within a polyethylene glycol conformal coating as described in U.S. Pat. No. 5,529,914 prior to implantation.

The neurotrophic peptides of the invention may also be enclosed in micelles or liposomes. Liposome encapsulation technology is well known. Liposomes may be targeted to specific tissue, such as neural tissue, through the use of receptors, ligands or antibodies capable of binding the targeted tissue. The preparation of these formulations is well known in the art (Radin et al., *Meth. Enzymol.*, 98:613–618, 1983).

There are currently no available pharmaceuticals able to promote full functional regeneration and restoration of the structural integrity of neural systems. This is particularly true of the CNS. Regeneration of peripheral nerves through the use of neurotrophic factors is within the scope of this invention. Moreover, neurotrophic factors can be therapeutically useful in the treatment of neurodegenerative diseases associated with the degeneration of neural populations or specific areas of the brain. The principal cause of Parkinson's disease is the degeneration of dopaminergic neurons of the substantia nigra. Since antibodies against prosaposin immunohistochemically stain the dopaminergic neurons of the substantia nigra in human brain sections, the RI peptides of the invention may be therapeutically useful in the treatment of Parkinson's disease. Retinal neuropathy, an ocular neurodegenerative disorder leading to loss of vision in the elderly, is also treatable using the RI peptides of the invention.

It has long been believed that in order to reach neuronal populations in the brain, neurotrophic factors would have to be administered intracerebrally since these proteins do not cross the blood brain barrier. U.S. Pat. No. 5,571,787 discloses that an iodinated neurotrophic 18-mer fragment derived from saposin C crosses the blood brain barrier. Thus, the RI peptides having up to about 22 amino acids will also cross this barrier and can thus be administered intravenously. Other neuronal populations, such as motor neurons, can also be treated by intravenous injection, although direct injection into the cerebrospinal fluid is also envisioned as an alternate route.

Cells may be treated to facilitate myelin formation or to prevent demyelination in the manner described above in vivo, ex vivo or in vitro. Diseases resulting in demyelination of nerve fibers including MS, acute disseminated leukoencephalitis, trauma to brain and/or spinal cord, progressive multifocal leukoencephalitis, metachromatic leukodystrophy, adrenal leukodystrophy and maldevelopment of the white matter in premature infants (periventricular leucomalacia) can be slowed or halted by administration of the neurotrophic peptides of the invention to the cells affected by the disease.

The compositions of the present invention can be used in vitro as research tools for studying the effects of neurotrophic factors and myelin facilitating materials. However, more practically, they have an immediate use as laboratory reagents and components of cell growth media in order to facilitate growth and maintain neural cells in vitro.

The peptides of the invention are synthesized using an automated solid-phase protocol well known in the art on an Applied Biosystems Model 430 peptide synthesizer. All peptides were purified by high performance liquid chromatography (HPLC) on a Vydac C4 column to an extent greater than 95% prior to use.

The following examples are merely illustrative and are not intended to limit the scope of the present invention.

EXAMPLE 1
Stimulation of Neurite Outgrowth

NS20Y neuroblastoma cells were grown in DMEM containing 10% fetal calf serum (FCS). Cells were removed with trypsin and plated in 30 mm petri dishes onto glass coverslips. After 20–24 hours, the medium was replaced with 2 ml DMEM containing 0.5% FCS plus 0, 0.5, 1, 2, 4 or 8 ng/ml effector peptides. Cells were cultured for an additional 24 hours, washed with PBS and fixed with Bouin's solution (saturated aqueous picric acid/formalin/acetic acid 15:5:1) for 30 minutes. Fixative was removed with PBS and neurite outgrowth was scored under a phase contrast microscope. Cells exhibiting one or more clearly defined neurites equal to or longer than one cell diameter were scored as positive. At least 200 cells were scored in different portions of each dish to determine the percentage of neurite bearing cells and assays were performed in duplicate.

As shown in FIGS. 1 and 3, TX14(A) (SEQ ID NO: 4), the RI TX14(A) (peptide D2; SEQ ID NO: 5), the rat 14-mer (SEQ ID NO: 6), peptide D4 (SEQ ID NO: 7) and peptide D5 (SEQ ID NO: 8) all induced neurite outgrowth in NS20Y cells. Increased neurite outgrowth was evident using as little as 0.5 ng/ml peptide. D2, the rat 14-mer and TX14(A) stimulated neurite outgrowth to similar extents at 8 ng/ml, although D2 was slightly more effective than TX14(A). This indicates that the RI peptides have neurotrophic activity.

EXAMPLE 2
Prevention of Cell Death

NS20Y cells were plated as described in Example 1 and grown on glass coverslips in 0.5% fetal bovine serum for 2 days in the presence or absence of 8 ng/ml effector peptides. Media was removed and 0.2% trypan blue in PBS was added to each well. Blue-staining dead cells were scored as a percentage of the total on an inverted microscope, counting 400 cells in four areas of each well. The average error of duplicates was ±5%. As shown in FIG. 2, both TX14(A) and D2 reduced the number of trypan blue-positive (dead) cells by about 50%. This indicates that both the RI and wild type peptides can rescue neural cells from cell death.

EXAMPLE 3
Promotion of Neurite Outgrowth ex vivo

Figure 4:
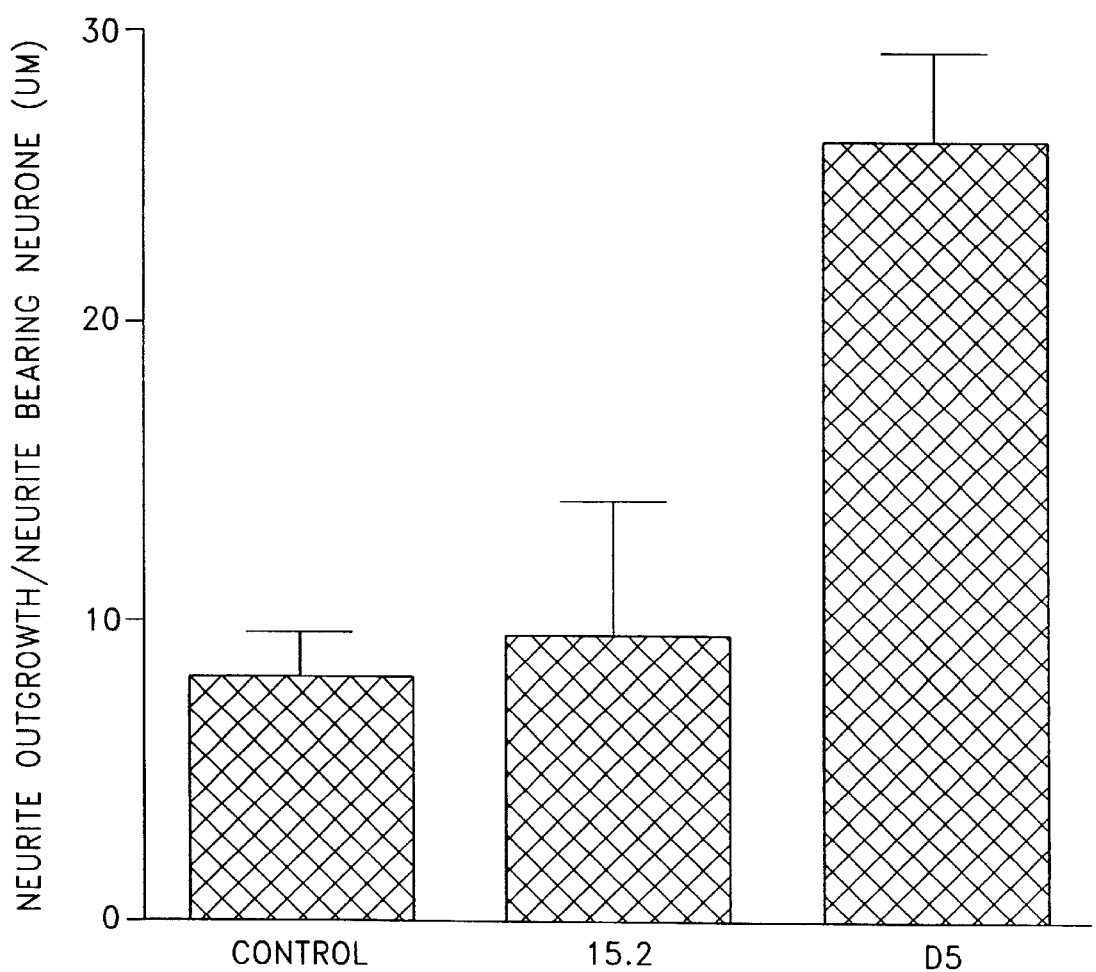
FIG. 4 shows the effects of peptide D5 and peptide 15-2 (TXLIDNNKTEKEILY; X=D-alanine; SEQ ID NO: 9) on ex vivo adult rat sensory neurite outgrowth.

Dorsal root ganglia were removed from adult rats and sensory neurons were prepared as described by Kuffler et al. (*J. Neurobiol.* 25:1267–1282, 1994). Neurons were treated with 0.5 ng/ml peptide 15-2 or peptide D5. After three days of treatment, the length of the longest neuritic projections were measured on a micrometer grid. The longest neurites in neurons treated with peptide D5 were approximately three times longer than those treated with a control (non-RI) peptide (15-2) or in untreated controls (FIG. 4). After a 48 hour treatment, all cells responded similarly to nerve growth factor (NGF) in that extensive branching was observed. These results indicate that peptide D5 promotes the differentiation of sensory neurons.

EXAMPLE 4
Localization and Integrity of Peptide D4 after Injection

Peptide D4 (SEQ ID NO: 7) was iodinated at the terminal tyrosine residue with $^{125}$I according to the manufacturer's instructions (Pierce Chemical Co., Rockford, Ill.), and 200 μg/kg in PBS was injected intramuscularly into an adult male Sprague-Dawley rat. After 20 min., the rat was anesthetized, perfused with PBS and the organs removed and counted in a gamma counter. Results below give ng/g of D4 in each tissue after conversion of cpm to nanograms (Table 1). Concentrations in brain are approximately 20 times higher than the required neurotrophic dose for neural cells determined in vitro.

Figure 5:
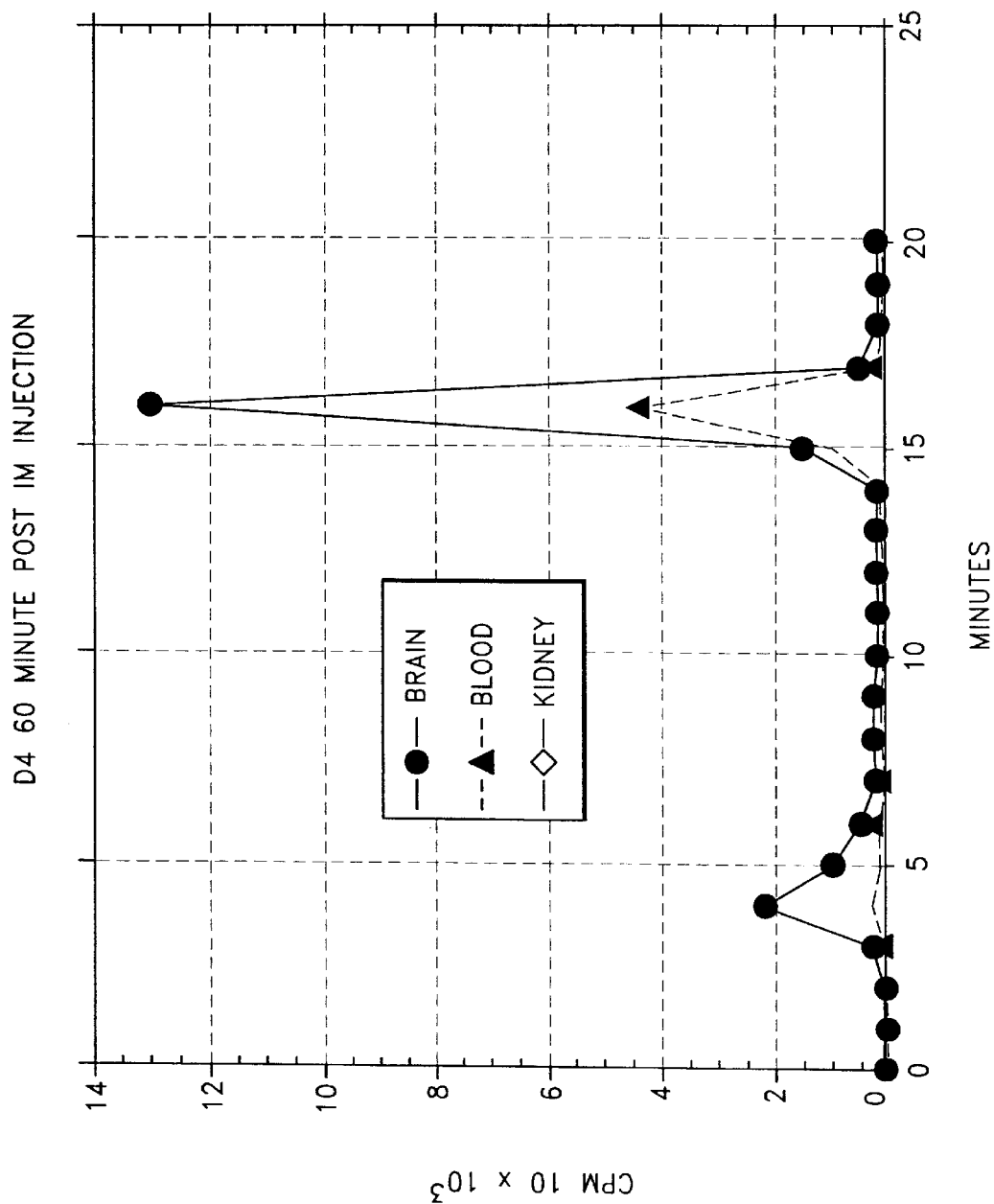
FIG. 5 is a graph showing the levels of iodinated peptide D4 60 minutes after intramuscular injection into an adult rat.

In another study, an aliquot of brain, liver, lung and kidney was taken 60 minutes after injection for HPLC analyses (Vydac C4 column) to determine the integrity (intactness) of the peptide in brain, blood and kidney. Peptide D4 was 95% intact in these organs, indicating the in vivo stability of this peptide after 60 minutes. The amount of peptide D4 present in the brain, blood and kidney 60 minutes after $^{125}$I-D4 injection is shown in FIG. 5. The peak at 16 min. is intact D4; a breakdown product peak is evident at 4 min. These results indicate that D4 is stable in vivo and crosses the blood brain barrier in amounts sufficient to exert a therapeutic effect. In vitro studies demonstrate that 15 min. of exposure is sufficient to induce neurite outgrowth and rescue neural cells from death.

TABLE 1

| Organ | ng $^{125}$I-D4/gm wet wt. after 20 min. |
|---|---|
| Brain | 2.7 |
| Sciatic nerve | 379 |
| Lung | 130 |
| Heart | 35 |
| Liver | 19 |
| Spleen | 58 |
| Kidney | 800 |
| Skeletal | — |
| urine | intact |
| serum | intact |

EXAMPLE 5
Reversal of Demyelination in a Rat Model

Experimental allergic encephalomyelitis (EAE) is a rat model of human multiple sclerosis (MS). In rats, EAE is induced by injecting foreign protein (guinea pig spinal cord) which results in inflammation and demyelination in white matter 11 days later. This demyelination resembles that seen in actively demyelinating human MS lesions (Liu et al., *Multiple Sclerosis* 1:2–9, 1995).

EAE was induced in Lewis rats by injection of an emulsion of guinea pig spinal cord and complete Freund's adjuvant (CFA). At day 14, when weakness was evident, treatment with D5 (SEQ ID NO: 8) was begun (200 μg/kg intramuscularly) and continued for 8 days every day. Six rats were injected with vehicle only. Stride length, a measure of muscle weakness, was scored on days 14 and 22. In addition, the number and size of demyelinating lesions (plaques) in the spinal cord at day 22 per mm$^2$ was scored. Lastly, the amount of cholesterol ester in brain, a marker of myelin breakdown, was scored at day 22. The results are summarized in FIGS. 6–11.

Figure 6:
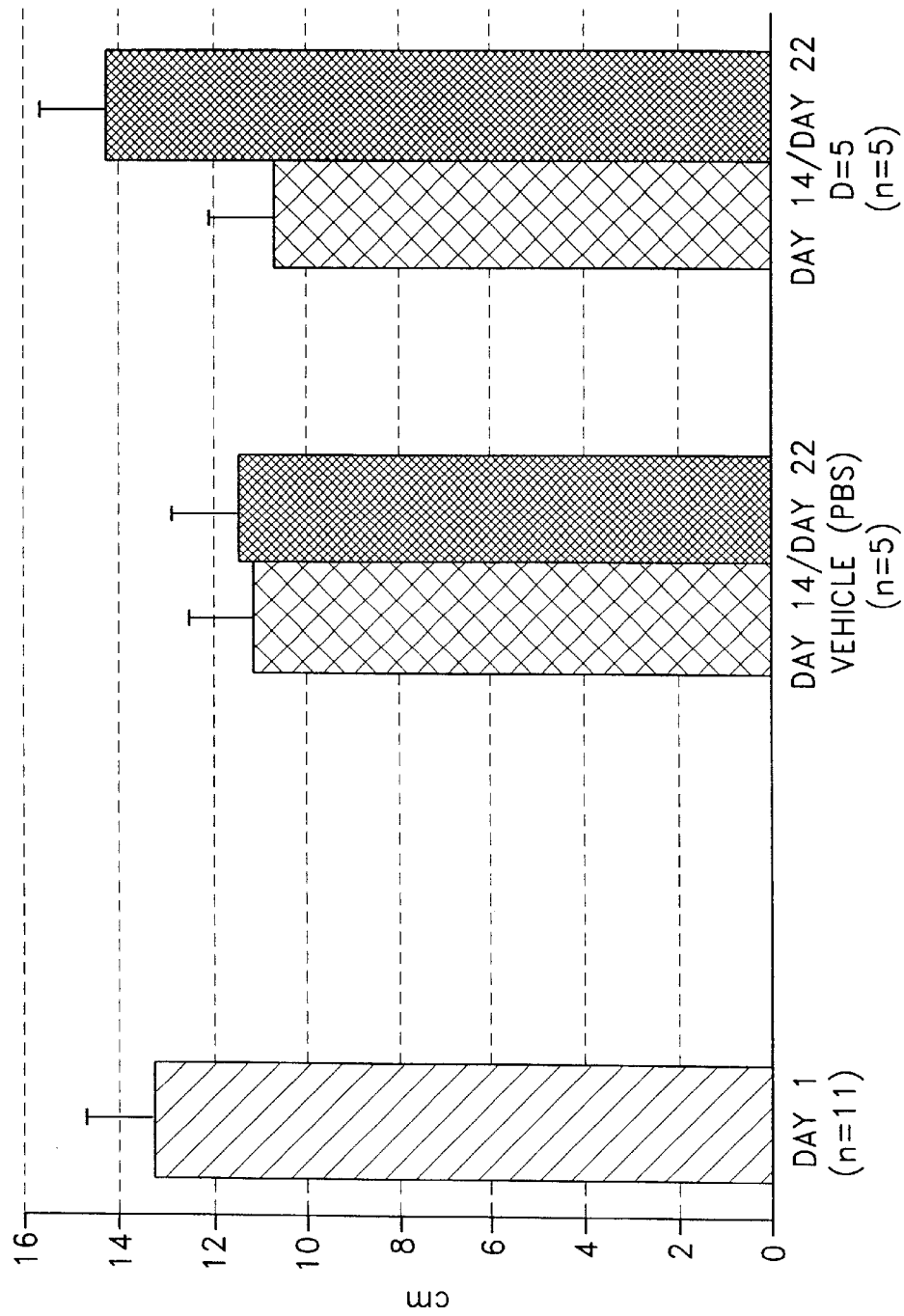
FIG. 6 is a graph showing the stride length in the Lewis Rat experimental allergic encephalomyelitis (EAE) model in animals treated with peptide D5 and in control animals.
Figure 7:
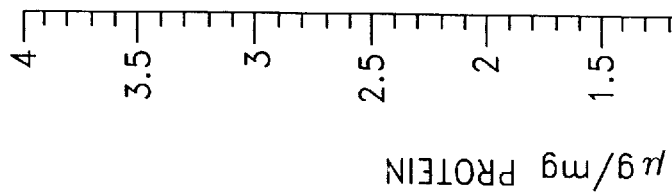
FIG. 7 is a graph showing cholesterol ester content in brain in the Lewis Rat EAE model treated with peptide D5 (200 µg/kg) intramuscularly for 8 days.
Figure 8:
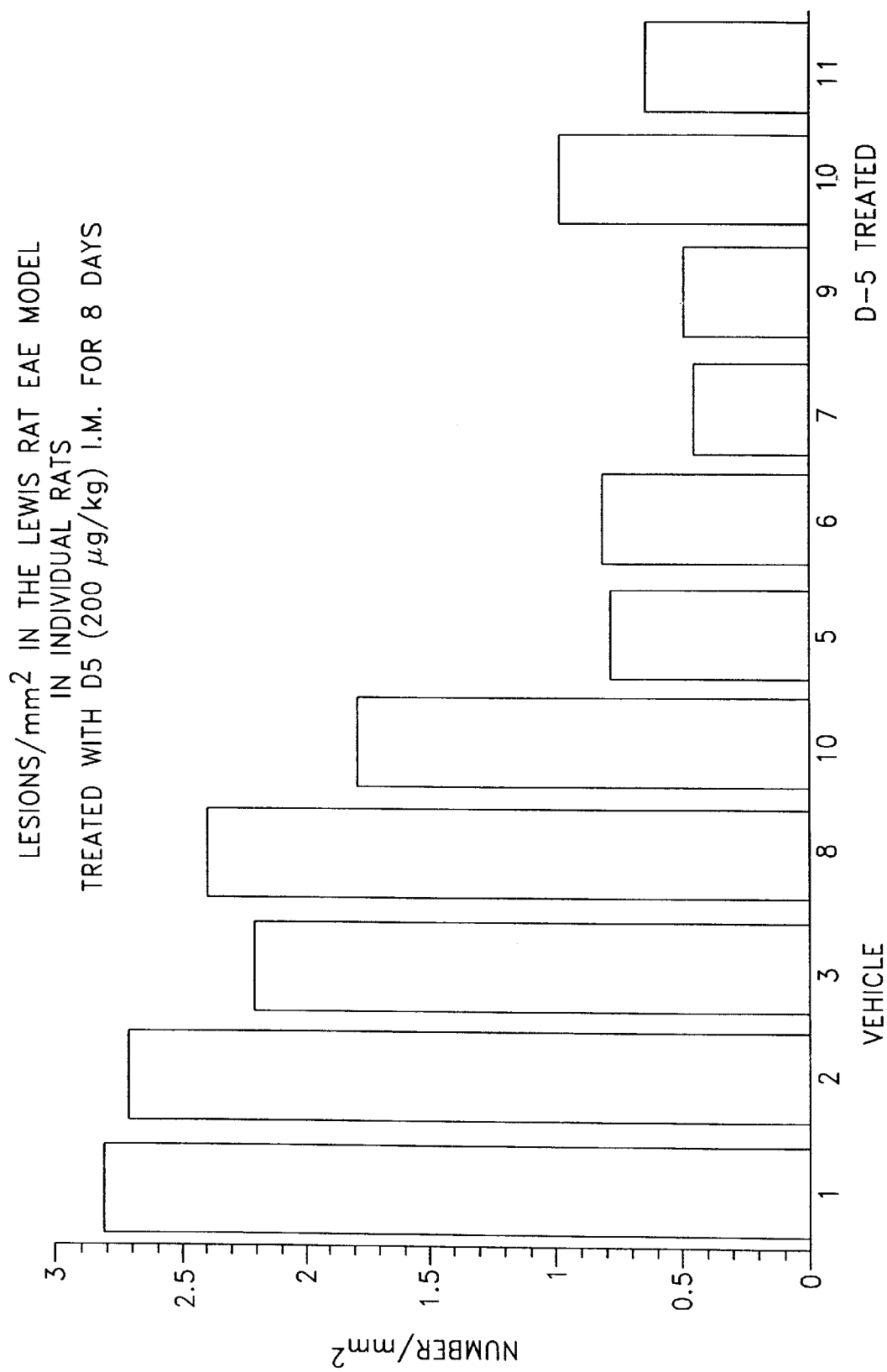
FIG. 8 is a graph showing the number of demyelinating lesions in the spinal cord/mm$^2$ in the Lewis Rat EAE model in individual rats treated with peptide D5 (200 µg/kg) intramuscularly for 8 days.
Figure 9:
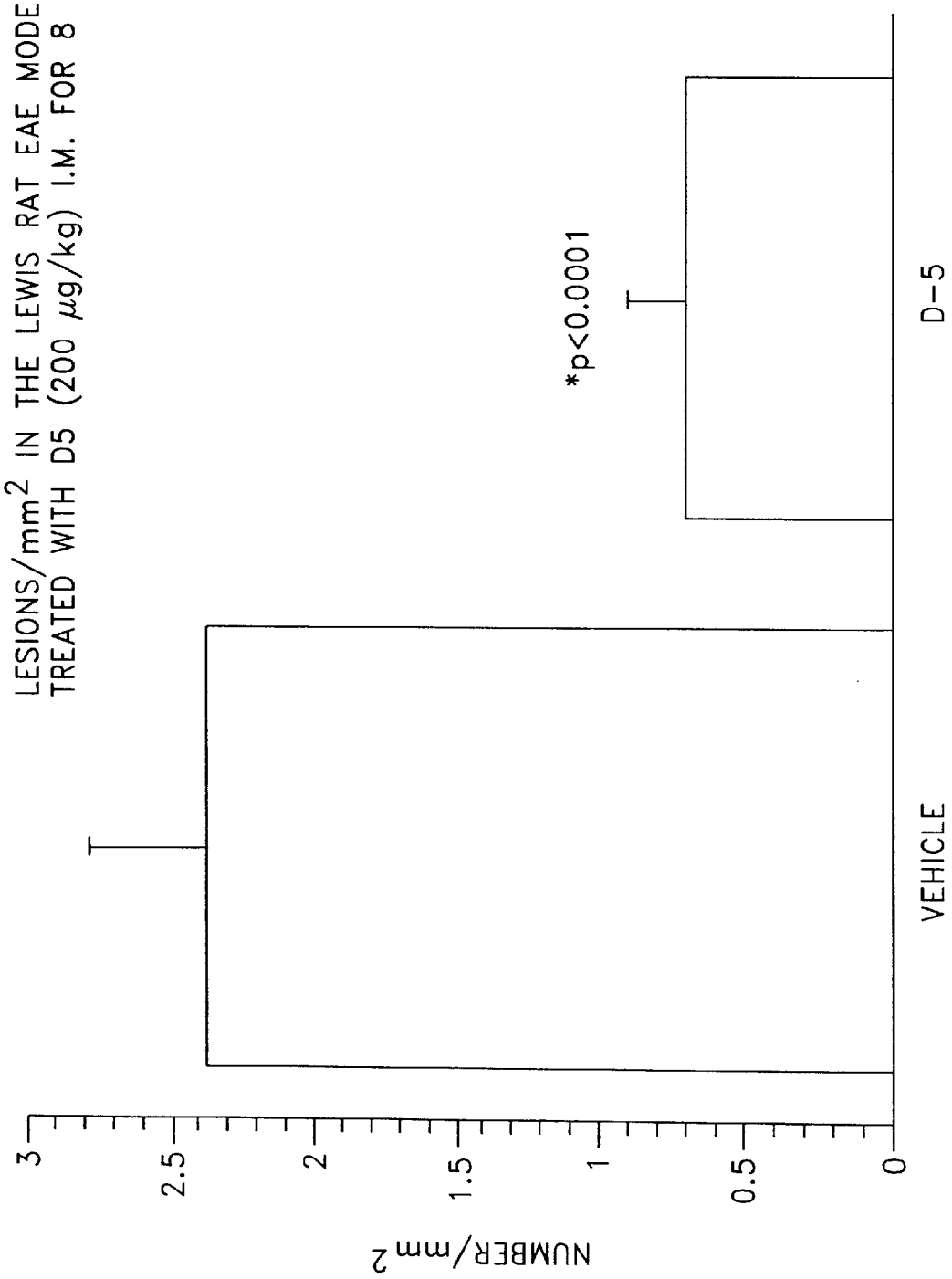
FIG. 9 is a graph showing the average number of lesions/mm$^2$ in the Lewis rat EAE model treated with peptide D5 (200 µg/kg) intramuscularly for 8 days.

As shown in FIG. 6, the stride length of both groups were decreased at day 14, wherease after treatment for 8 days, the D5-treated animals returned to normal, but the vehicle treated animals did not (p<0.018). As shown in FIG. 7, a significant reduction of cholesterol ester content was observed in the brains of the treated group. Moreover, as shown in FIGS. 8 and 9, the number of spinal cord lesions was reduced by 70% after 10 days of treatment with D5.

Figure 10:
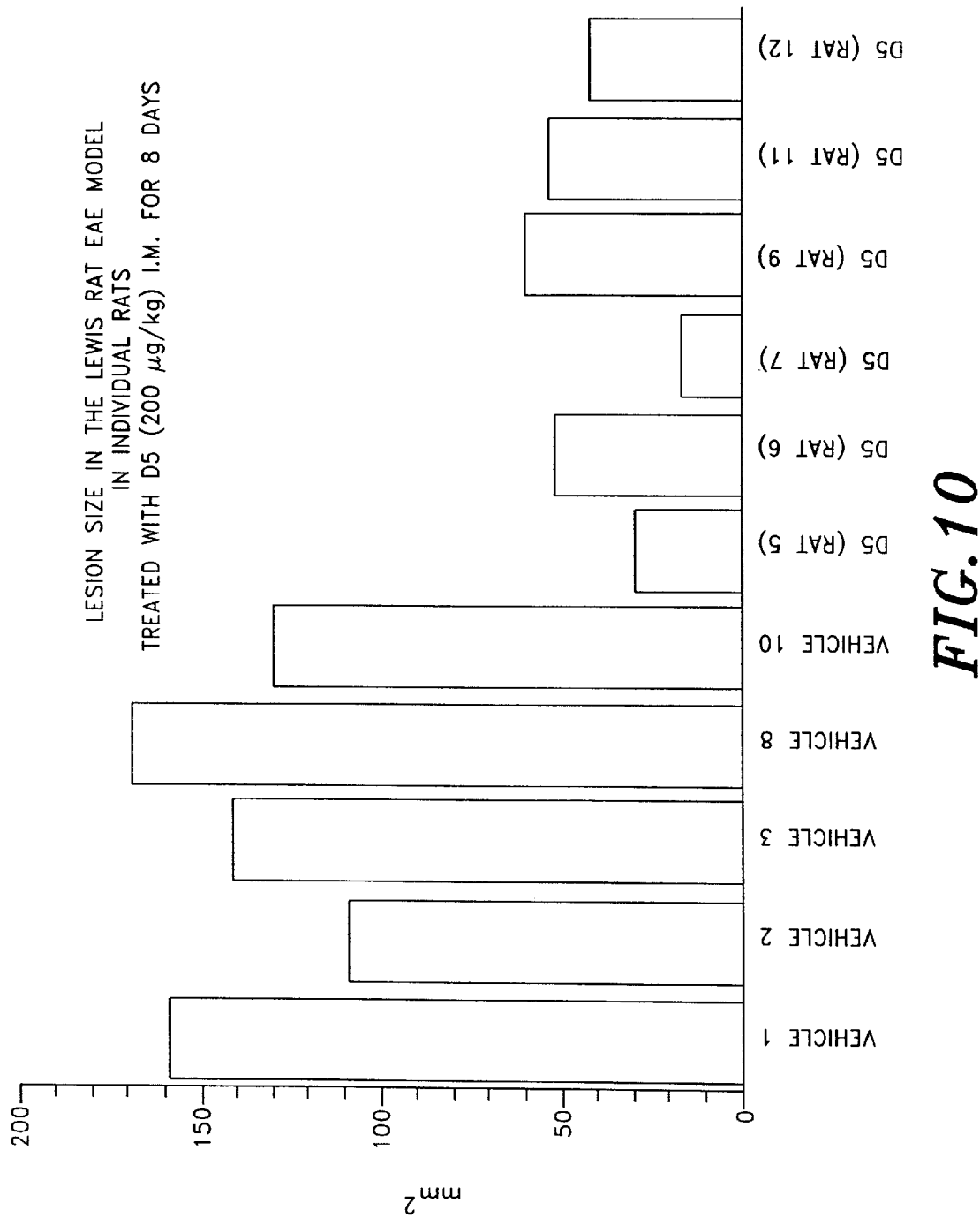
FIG. 10 is a graph showing the lesion size in the Lewis Rat EAE model in individual rats treated with D5 (200 µg/kg) intramuscularly for 8 days.
Figure 11:
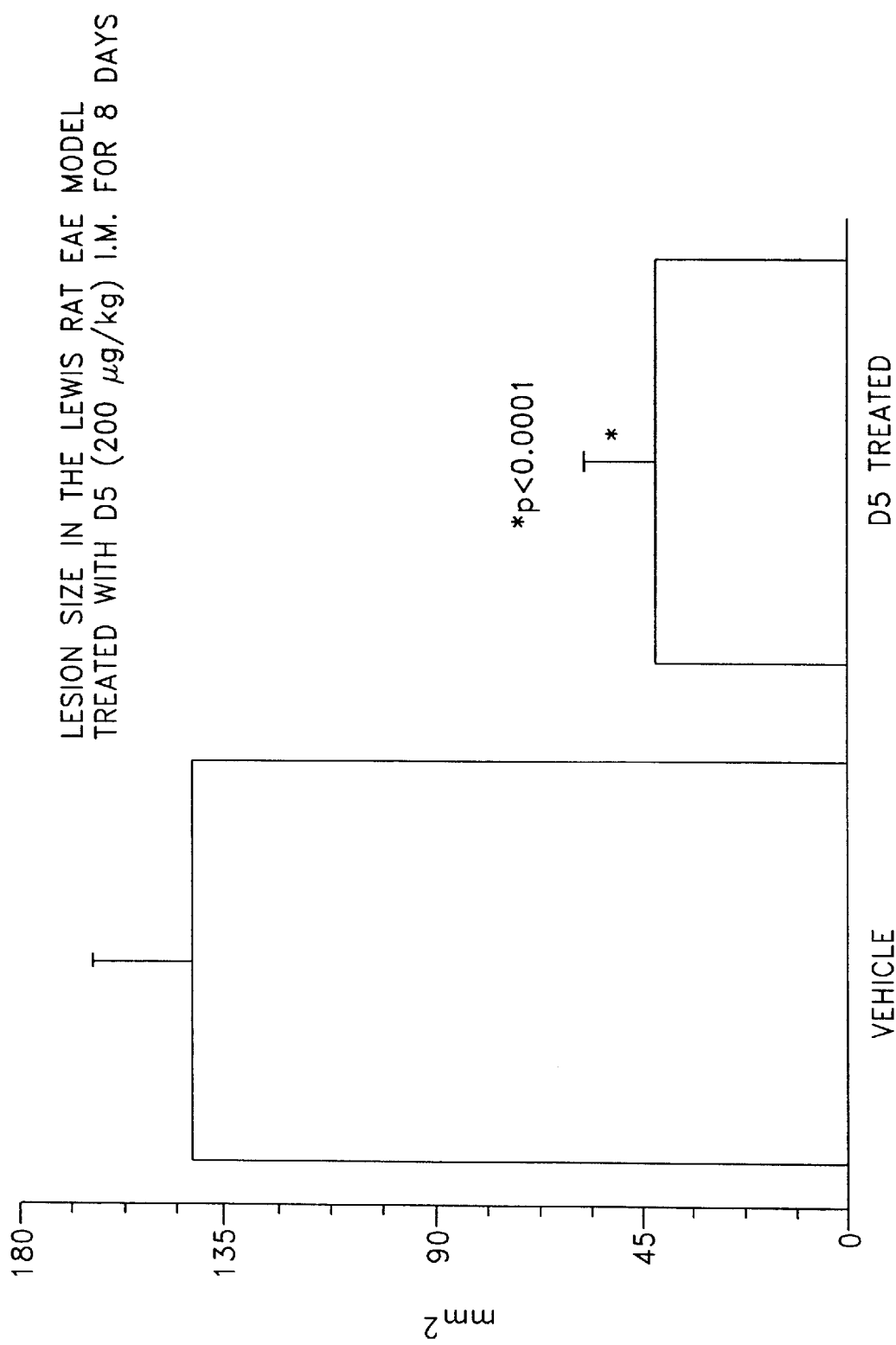
FIG. 11 is a graph showing the average lesion size in the Lewis Rat EAE model in individual rats treated with D5 (200 µg/kg) intramuscularly for 8 days.

Lastly, as shown in FIGS. 10 and 11, the average lesion size was reduced by about 70%. There was no difference in weight loss between the control and experimental animals. These results indicate a significant clinical, biochemical and morphological reversal of EAE after systemic treatment with D5. This action differs from the anti-inflammatory effect of current MS drugs which do not act directly upon myelin repair.

EXAMPLE 6
Ex vivo Myelination Assay

Newborn mouse cerebellar explants are prepared according to Satomi (*Zool. Sci.* 9:127–137, 1992). Neurite outgrowth and myelination are observed for 22 days in culture, during the period when the newborn mouse cerebellum normally undergoes neuronal differentiation and myelination begins. D2, D3, D4, D5 or another peptide including SEQ ID NO: 12 is added on the second day after preparation of the explants (three control and three treated explants) and outgrowth of neurites and myelination are assessed under a bright field microscope with a video camera. Saposin C is used as a positive control at a concentration of between about 1 and 10 μg/ml. Myelination is stimulated by D2, D3, D4, D5 or another peptide including SEQ ID NO: 12 to a similar extent as with saposin C.

Alternatively, myelination may be assayed by incorporation of $^{35}S$ into sulfolipids which are exclusive to myelin as described below.

EXAMPLE 7
Incorporation of $^{35}S$ into Sulfolipids

Primary myelin-containing Schwann cells are incubated in low sulfate media (DMEM) containing 0.5% fetal bovine serum (FBS), followed by addition of $^{35S}$-methionine and peptide D2, D3, D4, D5 or another peptide including SEQ ID NO: 12 for 48 hours. Saposin C is used as a positive control. Cells are rinsed with PBS, harvested and sonicated in 100 μl distilled water. An aliquot of cell lysate is removed for protein analysis and the remainder is extracted with 5 ml chloroform/methanol (2:1, v/v). Lipid extracts are chromatographed and immunostained with anti-sulfatide monoclonal antibody as described (Hiraiwa et al., *Proc. Natl. Acad. Sci. U.S.A.* 94:4778–4781). Similar amounts of sulfatide are observed after D2 or peptide including SEQ ID NO: 12 and saposin C treatment.

EXAMPLE 8
Use of RI Peptides in Treating Traumatic Ischemic CNS Lesions

Humans with traumatic lesions to the brain or spinal cord receive systemic injections of about 100 μg/kg peptide D2, D3, D4, D5 or another peptide including SEQ ID NO: 12 in a sterile saline solution or in depot form. Improvement is assessed by gain of sensory or motor nerve function (i.e. increased limb movement). Treatments continue until no further improvement occurs.

EXAMPLE 9
Use of RI Peptides in Treating Demyelination Disorders

Patients diagnosed with early stage MS are given peptide D2, D3, D4, D5 or other peptide including SEQ ID NO: 12 by systemic injection using the same dose range as in Example 8. Dosages are repeated daily or weekly and improvement in muscle strength, musculoskeletal coordination and myelination (as determined by MRI) is observed. Patients with chronic relapsing MS are treated in the same manner when subsequent relapses occur.

EXAMPLE 10
Alleviation of Neuropathic Pain in Chunk Model Rats

This example describes the effects of bolus intrathecal injection of peptides shown D2, D3, D4, D5 or another peptide including the sequence shown in SEQ ID NO: 12 in the Chung experimental model of peripheral neuropathic pain. Each of the four peptides is chemically synthesized, purified, dissolved in sterile PBS and buffered to neutral pH. The surgical procedure previously described by Kim et al. (*Pain*, 50:355–363, 1992) is performed on male rats to induce an allodynic state. A spinal catheter is introduced two weeks after surgery, Five days later, the peptides are administered at 0.007, 0.07 and 0.7 μg/rat. Pressure thresholds are then determined using calibrated von Frey hairs. The longer the time taken for an animal to withdraw the paw in response to applied pressure, the less severe the neuropathic pain. The peptides significantly increase the threshold pressure, indicating a significant alleviation of neuropathic pain.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A peptide comprising SEQ ID NO:5.
2. A peptide comprising SEQ ID NO:6.
3. A peptide comprising SEQ ID NO:7.
4. A peptide comprising SEQ ID NO:8.
5. A peptide comprising SEQ ID NO:9.
6. A peptide comprising SEQ ID NO:11.
7. The peptide of claims 1–6, wherein said peptide is modified at the amino terminus, carboxy terminus, or both amino and carboxy terminus with a moiety independently selected from the group consisting of $CH_3CO$, $CH_3(CH_2)_nCO$, $C_6H_5CH_2CO$ and $H_2N(CH_2)_n$ wherein n=1–10.
8. The peptide of claims 1–6, wherein said peptide is glycosylated at Asn7 or at the alpha amino group.
9. The peptide of claims 1–6, wherein one or more amide bonds thereof is reduced.
10. The peptide of claims 1–6, wherein one or more nitrogens in said peptide is methylated.
11. The peptide of claims 1–6, wherein one or more carboxylic acid groups in said peptide is esterified.
12. A composition comprising a peptide consisting essentially of SEQ ID NO:5.
13. A composition comprising a peptide consisting essentially of SEQ ID NO:6.
14. A composition comprising a peptide consisting essentially of SEQ ID NO:7.
15. A composition comprising a peptide consisting essentially of SEQ ID NO:8.
16. A composition comprising a peptide consisting essentially of SEQ ID NO:9.
17. A composition comprising a peptide consisting essentially of SEQ ID NO:11.
18. The composition of claims 12–17, wherein said peptide is modified at the amino terminus, carboxy terminus, or both amino and carboxy terminus with a moiety independently selected from the group consisting of $CH_3CO$, $CH_3(CH_2)_nCO$, $C_6H_5CH_2CO$ and $H_2N(CH_2)_n$ wherein n=1–10.
19. The composition of claims 12–17, wherein said peptide is glycosylated at Asn7 or at the alpha amino group.
20. The composition of claims 12–17, wherein one or more amide bonds thereof is reduced.
21. The composition of claims 12–17, wherein one or more nitrogens in said peptide is methylated.
22. The composition of claims 12–17, wherein one or more carboxylic acid groups in said peptide is esterified.
23. The composition of claims 12–17, in a septum sealed vial.
24. The composition of claims 12–17, in a controlled release formulation.
25. The composition of claims 12–17, in liposomal form.
26. The composition of claims 12–17, in lyophilized form.
27. The composition of claims 12–17, in unit dosage form.
28. The composition of claims 12–17, wherein said composition is a pharmaceutical.

* * * * *